United States Patent
Rosenberg

(10) Patent No.: US 10,099,528 B2
(45) Date of Patent: Oct. 16, 2018

(54) WHEEL HEIGHT ADJUSTMENT ASSEMBLY AND METHODS OF MAKING AND USING SAME

(71) Applicant: Jeff Rosenberg, Broken Arrow, OK (US)

(72) Inventor: Jeff Rosenberg, Broken Arrow, OK (US)

( * ) Notice: Subject to any disclaimer, the term of this patent is extended or adjusted under 35 U.S.C. 154(b) by 10 days.

(21) Appl. No.: 15/428,400

(22) Filed: Feb. 9, 2017

(65) Prior Publication Data

US 2018/0222269 A1    Aug. 9, 2018

(51) Int. Cl.
*B60G 17/00* (2006.01)
*G01N 27/87* (2006.01)

(52) U.S. Cl.
CPC ............. *B60G 17/00* (2013.01); *G01N 27/87* (2013.01); *B60G 2300/00* (2013.01)

(58) Field of Classification Search
CPC ...... B60G 17/00; B60G 2300/00; B62D 7/18; G01N 27/87
See application file for complete search history.

(56) References Cited

U.S. PATENT DOCUMENTS

| | | | | |
|---|---|---|---|---|
| 2,828,968 A * | 4/1958 | Engler | ............... | A01D 34/63 280/43 |
| 3,428,328 A * | 2/1969 | Dickson | ............... | A01D 34/74 280/43.17 |
| 5,020,310 A * | 6/1991 | Oshima | ............... | A01D 34/74 56/17.2 |
| 5,845,471 A * | 12/1998 | Seegert | ............... | A01D 34/74 56/17.2 |
| 8,141,651 B1 * | 3/2012 | Christianson | ......... | A01G 20/30 172/21 |
| 9,723,788 B2 * | 8/2017 | Bucharzewski | ..... | A01D 89/006 |

* cited by examiner

*Primary Examiner* — Faye M Fleming
(74) *Attorney, Agent, or Firm* — Hall Estill Law Firm

(57) ABSTRACT

The present disclosure is directed to a wheel height adjustment assembly. The wheel height adjustment assembly includes a mounting bracket, a tapered insert, a drawbar and a wheel connected together. The mounting bracket has a first end, a second end and a sidewall. A tapered opening is formed in the sidewall of the mounting bracket for receiving the tapered insert. The tapered insert has a first end, a second end a body portion positioned between the first end and the second end. The first end and the second end are provided with threaded openings. The openings are offset from one another.

17 Claims, 3 Drawing Sheets

WHEEL HEIGHT ADJUSTMENT ASSEMBLY AND METHODS OF MAKING AND USING SAME

CROSS-REFERENCE TO RELATED APPLICATIONS

Not applicable.

FIELD OF THE INVENTION

The present disclosure relates generally to a wheel height adjuster on a device, and more particularly, not by way of limitation, to an improved assembly for adjusting the wheel height on a device.

BACKGROUND OF THE INVENTION

Magnetic flux leakage above ground tank floor inspection devices (scanners) have been around for 20+ years. These devices use very strong magnets to saturate a section of a typically coated steel tank floor. This means the scanner is firmly held against the steel floor by the magnets with a force in hundreds of pounds.

The scanners are suspended away from the tank floor with four wheels. The wheels need to be pulled away from the tank floor and repositioned numerous times. This is typically accomplished by tilting the scanner back on the rear wheels using the leverage of a long handle. The rear wheels support much more than the weight of the inspection process. Then the scanner is moved to a new location and lowered to the tank floor. The scanner crashes against the tank floor because the strength of the magnetic field increases exponentially as it gets close to the tank floor. The front wheels need to absorb the crash force without changing the adjusted wheel height.

The wheel height needs to be different for different conditions like tank floor coating thickness, tank floor steel thickness, and wheel wear. In other words, the location of the wheels relative to the scanner body need to be adjusted. Existing inspection devices use some form of a screw or different sized wheels to set the wheel height.

The wheel height adjustment with a screw typically uses a screw to set the height and some clamping method to hold the position and keep forces from damaging the screw. There also needs to be some way to keep debris away from the screw threads. There are several scanners that use this adjustment technique but it is somewhat complex and has been prone to damage from operator errors.

Adjusting the wheel height with different sized wheels has multiple drawbacks: 1) the operator has to carry several sets of wheels for each height needed, 2) wheel wear changes the wheel height, and 3) the cost of having multiple wheels and having to replace them is expensive.

To this end, a need exists to allow the wheel height on a scanner to be adjusted and then easily resist the mechanical forces trying to change the wheel height during the inspection process of a tank floor. It is to such an assembly that the present disclosure is directed.

BRIEF DESCRIPTION OF THE DRAWING(S)

DETAILED DESCRIPTION OF THE INVENTION

Figure 1:
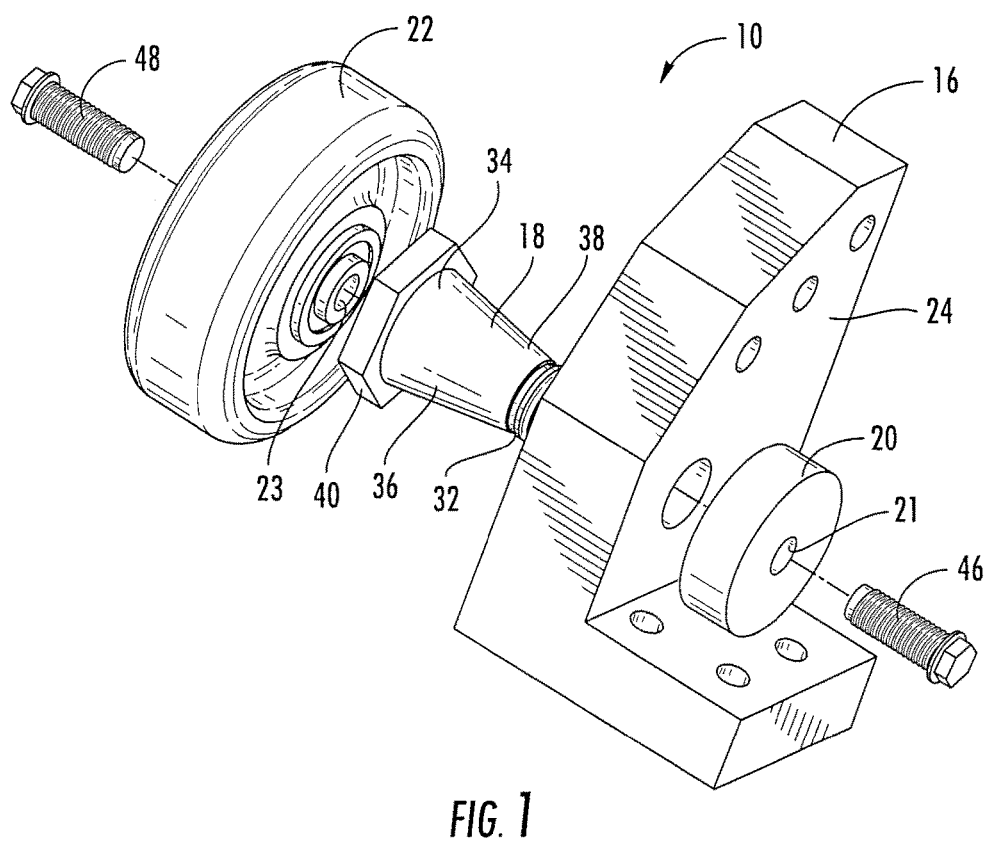
FIG. 1 is a perspective view of one embodiment of a wheel height adjustment assembly constructed in accordance with the present disclosure.
Figure 2:
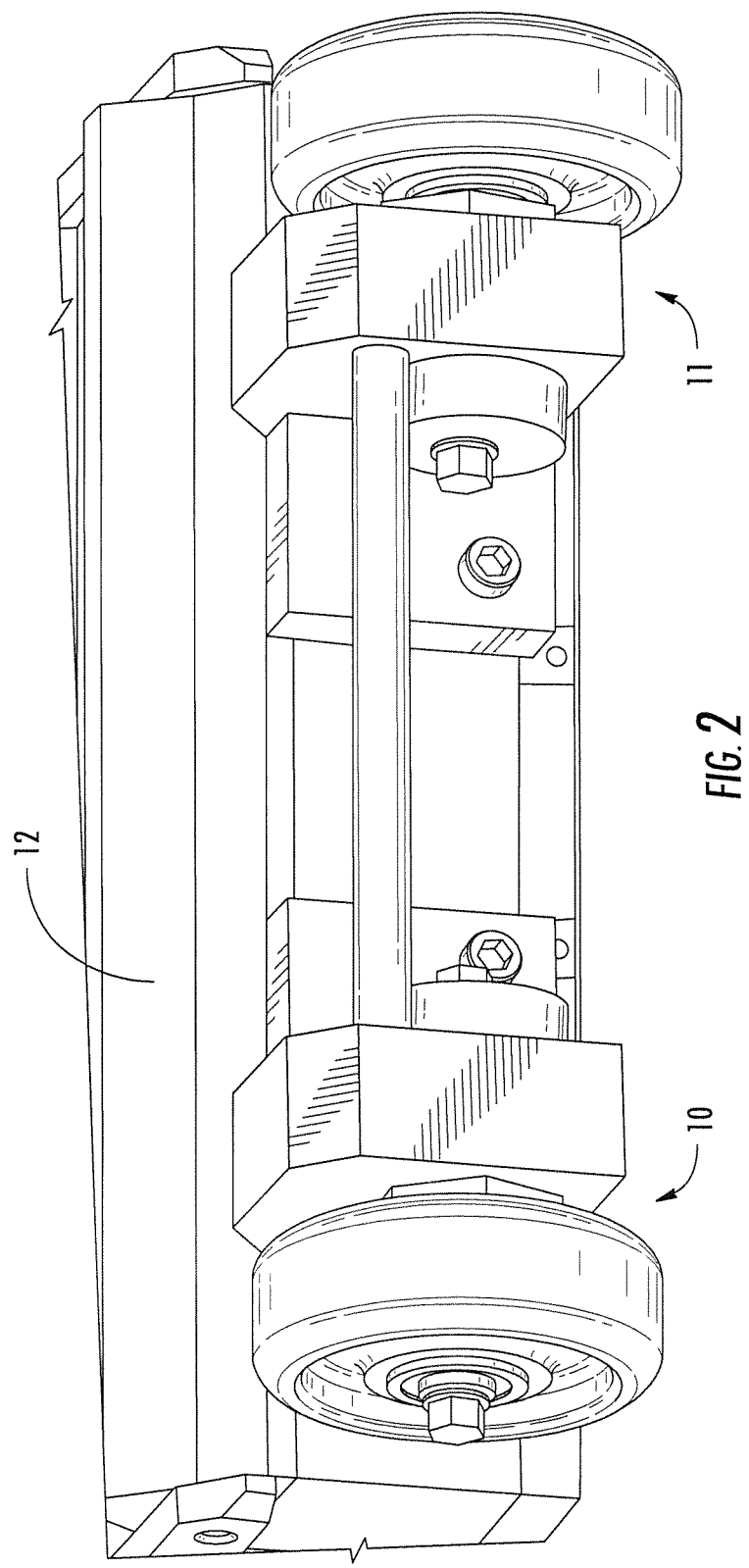
FIG. 2 is a perspective view of the wheel height adjustment assembly of FIG. 1 mounted to a scanner.
Figure 3:
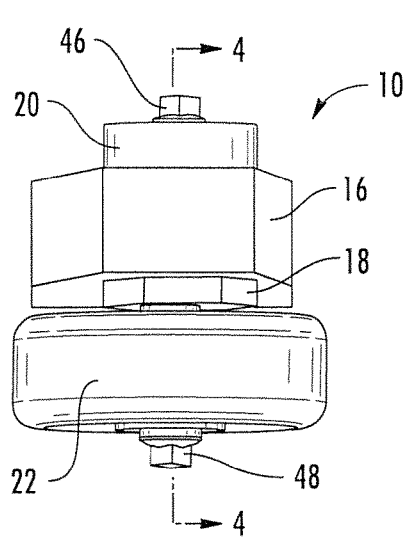
FIG. 3 is a side view of the wheel height adjustment assembly of FIG. 1.
Figure 4:
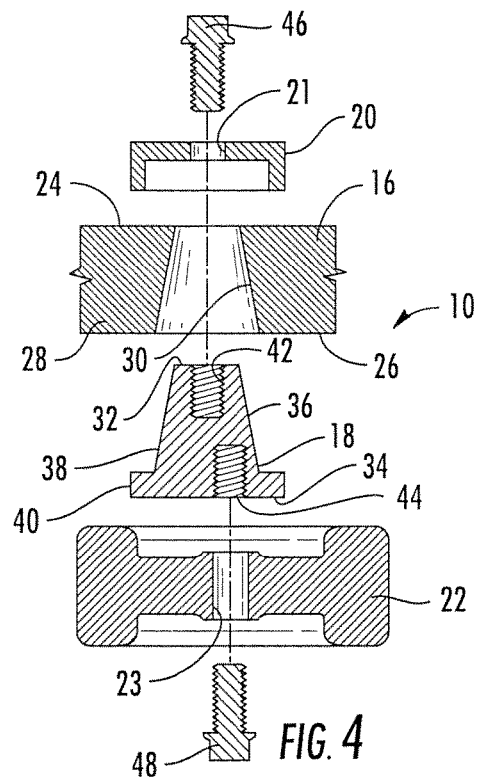
FIG. 4 is a cross-sectional view of the wheel height adjustment assembly of FIG. 3

Before explaining at least one embodiment of the inventive concept disclosed herein in detail, it is to be understood that the inventive concept is not limited in its application to the details of construction, experiments, exemplary data, and/or the arrangement of the components set forth in the following description, or illustrated in the drawings. The presently disclosed and claimed inventive concept is capable of other embodiments or of being practiced or carried out in various ways. Also, it is to be understood that the phraseology and terminology employed herein is for purpose of description only and should not be regarded as limiting in any way.

In the following detailed description of embodiments of the inventive concept, numerous specific details are set forth in order to provide a more thorough understanding of the inventive concept. However, it will be apparent to one of ordinary skill in the art that the inventive concept within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings, and more particularly to FIGS. 1-4, shown therein is one embodiment of a wheel height adjustment assembly 10 constructed in accordance with the inventive concepts disclosed herein, the wheel height adjustment assembly 10 being shown connected to a magnetic flux leakage above ground tank floor inspection device (scanner) 12. A pair of wheel height adjustment assemblies 10 and 11 are shown (FIG. 2) connected to a front of the scanner 12. The wheel height adjustment assemblies 10 and 11 are similar, only wheel height adjustment assembly 10 will be described. The scanner 12 is a common tool used for inspecting steel floors and is well known to one of ordinary skill in the art. Thus, no further discussion is necessary regarding the scanner 12 or its operation.

It is contemplated that the wheel height adjustment assembly 10 is constructed from various components, however, it should be understood that the wheel height adjustment assembly 10 may be constructed from one solid piece of material. The wheel height adjustment assembly 10 is preferably made of a durable and rigid material which is strong enough to prevent movement and bending of the wheel height adjustment assembly 10. Suitable materials for construction of the wheel height adjustment assembly 10 and components thereof include metals such as aluminum, steel, titanium, magnesium or alloys containing these metals, plastics, polymeric materials, and composite materials which are capable of providing the desired strength and durability for the wheel height adjustment assembly 10. It should be understood that the size and configuration of the wheel height adjustment assembly 10, and portions thereof, may vary widely dependent upon the size of the scanner 12. It should be understood by one of ordinary skill in the art that the wheel height adjustment assembly 10, although discussed herein as being used with a scanner 12, may be utilized and configured for use with adjusting the height of various devices.

In one embodiment, the wheel height adjustment assembly 10 includes a mounting bracket 16, a tapered insert 18, a drawbar 20 having an opening 21 and a wheel 22 with an opening 23. The mounting bracket 16 has a first end 24, a second end 26 and a sidewall 28. A tapered opening 30 is formed in the sidewall 28 of the mounting bracket 16 for receiving the tapered insert 18. The opening 30 extends between the first end 24 and the second end 26 of the mounting bracket 16. A portion of the mounting bracket 16 is mounted to the scanner 12 or other device. The mounting bracket 16 may be modified to be connected to a device such as when used as pairs of mounting brackets. It will be understood by one of ordinary skill in the art that the modification of the mounting bracket 16 may be performed by various methods known to connect one object to another. In another embodiment (not shown), a recessed tapered portion may be formed in a device for receiving the tapered insert of the wheel height adjustment assembly, thus not requiring a mounting bracket.

The tapered insert 18 has a first end 32, a second end 34, a body portion 36 positioned between the first end 32 and the second end 34 and an outer peripheral surface 38. The tapered insert 18 is conical in shape and tapers from the second end 34 to the first end 32. However, it should be understood that the tapered insert 18 or portions thereof may be any shape, such as circular, oval, square, rectangular, triangular, polygonal, quadrilateral, ellipsoidal and the like, for example.

The tapered insert 18 is further provided with an outwardly extending shoulder 40 supported on the second end 34 of the tapered insert 18. The outwardly extending shoulder 40 is hexagonal in shape. However, it should be understood that the outwardly extending shoulder 40 may be any polygonal in shape such as heptagonal, octagonal or the like.

Further, the first end 32 and the second end 34 are each provided with threaded openings 42 and 44. The openings 42 and 44 are offset from one another. The opening 42 is not on the centerline of the opening 44. Opening 42 is sized for receiving a first bolt 46 for securing the first end 32 of the tapered insert 18 positioned in the mounting bracket 16 to the drawbar 20. Opening 44 is sized for receiving a second bolt 48 for connecting the wheel and the second end 34 of the tapered insert 16.

In use, the second bolt 48 secures the wheel 22 to the tapered insert 18. The opening 44 is not on the central axis of the tapered insert 18. Wheel height is adjusted by rotating the tapered insert 18. Positioning the wheel center away from the center of the tapered insert 18 makes it act like an eccentric cam. The tapered insert 18 is placed into the tapered opening 30 of the mounting bracket 16. The first bolt 46 and the draw bar 20 are used to hold the tapered insert 18 in the mounting bracket 16. The outwardly extending shoulder 40 of the tapered insert 18 can be used to position the wheel height when the tapered insert 18 is placed in the tapered opening 30, before the first bolt 46 is tightened. Once the desired wheel position is determined, the first bolt 46 is tightened. Since the tapered insert 18 is positioned in the tapered opening 30, the tightening of the first bolt 46 binds the tapered insert 18 to the tapered opening 30 of the mounting bracket 16 together to resist severe torsional forces.

Figure 5:
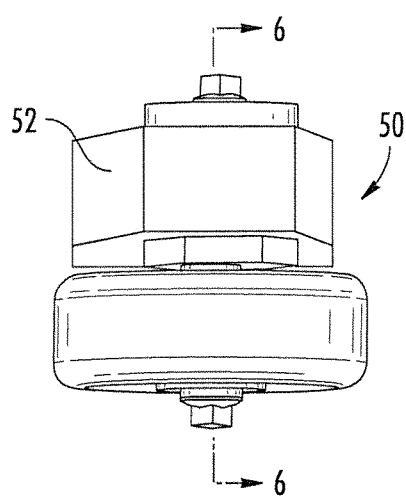
FIG. 5 is a side view of another embodiment a wheel height adjustment assembly constructed in accordance with the present disclosure.
Figure 6:
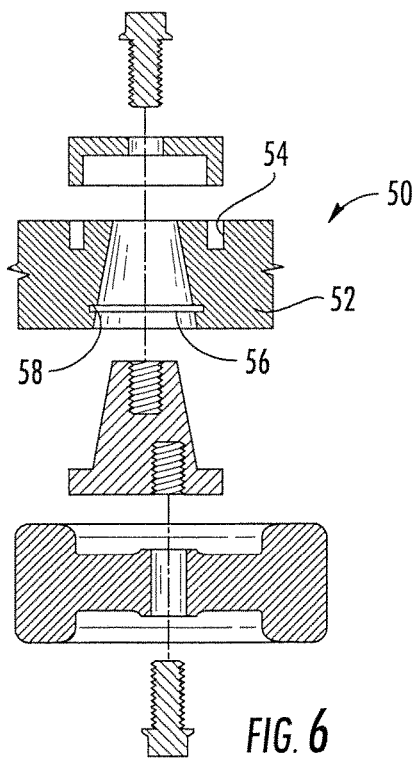
FIG. 6 is a cross-sectional view of the wheel height adjustment assembly of FIG. 5.

Referring now to FIGS. 5 and 6, another embodiment of a wheel height adjustment assembly 50 is shown. The wheel height adjustment assembly 50 is similar to the wheel height adjustment assembly 10 herein before described except as described hereinafter. That is, the wheel height adjustment assembly 50 includes a mounting bracket 52. The mounting bracket 52 is provided with a recessed area or annular slot 54, an o-ring groove 56 and o-ring 58. The recessed area 54 keeps the drawbar 20 aligned during the wheel adjustment process and prevents the wheel 22 from tilting during the wheel height adjustment. The o-ring 58 reduces the chance of dirt getting between the tapered insert 18 and the tapered opening 30 of the mounting bracket 16 during wheel height adjustment.

While the present invention is described herein utilized with a scanner, it should be understood by one of ordinary skill in the art the apparatus and methods of the present invention may be readily applied to use with other suitable devices.

From the above description, it is clear that the inventive concept(s) disclosed herein is well adapted to carry out the objects and to attain the advantages mentioned herein as well as those inherent in the inventive concept disclosed herein. While exemplary embodiments of the inventive concept disclosed herein have been described for purposes of this disclosure, it will be understood that numerous changes may be made which will readily suggest themselves to those skilled in the art and which are accomplished without departing from the scope of the inventive concept disclosed herein and defined by the appended claims.

What is claimed is:

1. A wheel height adjustment assembly for adjusting the wheel height of a device, comprising:
    a tapered insert having a first end, a second end and a tapered body portion positioned between the first end and the second end, the first end provided with a centrally located first opening and the second end provided with a second opening offset from the first opening, wherein the second end of the tapered insert is provided with an outwardly extending shoulder;
    a mounting bracket having a first end, a second end and a sidewall, a tapered opening being formed in the sidewall of the mounting bracket for receiving the tapered insert;
    a drawbar positioned on the first end of the mounting bracket connected to the tapered insert by the centrally located first opening; and
    a wheel connected to the tapered insert by the second opening.

2. The wheel height adjustment assembly of claim 1 wherein the mounting bracket includes a recessed area for receiving the drawbar.

3. The wheel height adjustment assembly of claim 1 wherein the mounting bracket includes an o-ring groove for receiving an o-ring.

4. The wheel height adjustment assembly of claim 1 wherein the drawbar is provided with an opening centered with the first opening of the tapered insert to facilitate the connection between the drawbar and the tapered insert.

5. The wheel height adjustment assembly of claim 1 further comprising:
   a first bolt to threadingly insert into the opening of the drawbar and the first opening of the tapered insert so as to threadingly connect the drawbar and the tapered insert.

6. The wheel height adjustment assembly of claim 1 wherein the wheel is provided with an opening centered with the second opening of the tapered insert to facilitate the connection between the wheel and the tapered insert.

7. The wheel height adjustment assembly of claim 1 further comprising:
   a second bolt to threadingly insert into the opening of the wheel and the second opening of the tapered insert so as to threadingly connect the wheel and the tapered insert.

8. A wheel height adjustment assembly for adjusting the wheel height of a device, comprising:
   a tapered insert having a first end, a second end and a tapered body portion positioned between the first end and the second end, the first end provided with a centrally located first opening and the second end provided with a second opening offset from the first opening;
   a mounting bracket having a first end, a second end and a sidewall, a tapered opening being formed in the sidewall of the mounting bracket for receiving the tapered insert, wherein the mounting bracket includes an o-ring groove for receiving an o-ring;
   a drawbar positioned on the first end of the mounting bracket connected to the tapered insert by the centrally located first opening; and
   a wheel connected to the tapered insert by the second opening.

9. A wheel height adjustment assembly for adjusting the wheel height of a device, comprising:
   a tapered insert having a first end, a second end and a tapered body portion positioned between the first end and the second end, the first end provided with a centrally located first opening and the second end provided with a second opening offset from the first opening;
   a mounting bracket having a first end, a second end and a sidewall, a tapered opening being formed in the sidewall of the mounting bracket for receiving the tapered insert;
   a drawbar positioned on the first end of the mounting bracket connected to the tapered insert by the centrally located first opening;
   a wheel connected to the tapered insert by the second opening; and
   a first bolt to threadingly insert into the opening of the drawbar and the first opening of the tapered insert so as to threadingly connect the drawbar and the tapered insert.

10. A wheel height adjustment assembly for adjusting the wheel height of a device, comprising:
    a cylindrical tapered insert having a first end, a second end and a tapered body portion positioned between the first end and the second end, the first end provided with a centrally located first opening and the second end provided with a second opening offset from the first opening;
    a mounting bracket having a first end, a second end and a sidewall, a tapered opening being formed in the sidewall of the mounting bracket;
    a drawbar positioned on the first end of the mounting bracket connected to the tapered insert by the centrally located first opening; and
    a wheel connected to the tapered insert by the second opening.

11. The wheel height adjustment assembly of claim 10 wherein the second end of the tapered insert is provided with an outwardly extending shoulder.

12. The wheel height adjustment assembly of claim 10 wherein the mounting bracket includes a recessed area for receiving the drawbar.

13. The wheel height adjustment assembly of claim 10 wherein the mounting bracket includes an o-ring groove for receiving an o-ring.

14. The wheel height adjustment assembly of claim 10 wherein the drawbar is provided with an opening centered with the first opening of the tapered insert to facilitate the connection between the drawbar and the tapered insert.

15. The wheel height adjustment assembly of claim 10 further comprising:
    a first bolt to threadingly insert into the opening of the drawbar and the first opening of the tapered insert so as to threadingly connect the drawbar and the tapered insert.

16. The wheel height adjustment assembly of claim 10 wherein the wheel is provided with an opening centered with the second opening of the tapered insert to facilitate the connection between the wheel and the tapered insert.

17. The wheel height adjustment assembly of claim 10 further comprising:
    a second bolt to threadingly insert into the opening of the wheel and the second opening of the tapered insert so as to threadingly connect the wheel and the tapered insert.

* * * * *